(12) United States Patent
Tass (10) Patent No.: US 8,116,874 B2
(45) Date of Patent: Feb. 14, 2012

(54) METHOD AND DEVICE FOR DESYNCHRONIZING NEURAL BRAIN ACTIVITY, CONTROLLER AND METHOD FOR TREATING NEURAL AND/OR PSYCHIATRIC DISORDERS

(75) Inventor: Peter Tass, Titz (DE)

(73) Assignee: Forschungzentrum Juelich GmbH, Juelich (DE)

(*) Notice: Subject to any disclaimer, the term of this patent is extended or adjusted under 35 U.S.C. 154(b) by 738 days.

(21) Appl. No.: 11/812,258

(22) Filed: Jun. 15, 2007

(65) Prior Publication Data
US 2008/0046025 A1  Feb. 21, 2008

Related U.S. Application Data

(63) Continuation of application No. PCT/DE2005/002192, filed on Dec. 6, 2005.

(30) Foreign Application Priority Data

Dec. 16, 2004 (DE) .......................... 10 2004 060514

(51) Int. Cl.
*A61N 1/18* (2006.01)

(52) U.S. Cl. .......................... 607/45; 607/115; 607/116

(58) Field of Classification Search .................. 600/378; 607/2, 45, 46, 48, 59, 115, 116, 139
See application file for complete search history.

(56) References Cited

U.S. PATENT DOCUMENTS

| | | | |
|---|---|---|---|
| 4,338,945 A | 7/1982 | Kosugi et al. | |
| 4,541,432 A | 9/1985 | Molina-Negro et al. | |
| 6,038,480 A | 3/2000 | Hrdlicka et al. | |
| 6,094,598 A | 7/2000 | Elsberry et al. | |
| 6,480,743 B1 * | 11/2002 | Kirkpatrick et al. | 607/45 |
| 6,529,774 B1 | 3/2003 | Greene | |
| 6,535,767 B1 | 3/2003 | Kronberg | |
| 6,671,557 B1 | 12/2003 | Gliner | |
| 6,944,501 B1 * | 9/2005 | Pless | 607/45 |
| 2002/0072770 A1 * | 6/2002 | Pless | 607/2 |
| 2002/0099418 A1 | 7/2002 | Naritoku et al. | |

(Continued)

FOREIGN PATENT DOCUMENTS

DE  102 11 765  10/2003

(Continued)

OTHER PUBLICATIONS

International Search Report dated Mar. 23, 2006 and issued in corresponding International Patent Application PCT/DE2005/002192.

(Continued)

*Primary Examiner* — Carl H Layno
*Assistant Examiner* — Jennifer Stewart (57) ABSTRACT

A device including at least one electrode and/or at least one chip configured to stimulate cerebral neurons that have a pathological oscillatory activity with a period duration T, n contact points that are distributed over at least one electrode and/or over at least one chip and are configured to output electrical stimulus signals to the brain, and a controller configured to drive the contact points so that the contact points output a low-frequency succession of sequences of high-frequency pulse trains to the brain, wherein, for each sequence, m contact points of the n contact points are selected, with m≧2 and m<n, and high-frequency pulse trains are applied only via the selected m points, and the temporal shift between two successive high-frequency pulse trains that are applied by different contact points is T/m.

7 Claims, 3 Drawing Sheets

U.S. PATENT DOCUMENTS

| | | | |
|---|---|---|---|
| 2003/0135248 A1 | 7/2003 | Stypulkowski | |
| 2004/0158298 A1* | 8/2004 | Gliner et al. | 607/48 |
| 2006/0212089 A1 | 9/2006 | Tass | |
| 2006/0276853 A1* | 12/2006 | Tass et al. | 607/45 |

FOREIGN PATENT DOCUMENTS

| | | |
|---|---|---|
| DE | 102 11 766 | 10/2003 |
| DE | 103 18 071 | 11/2004 |
| EP | 1 145 735 | 10/2001 |
| WO | 03-077986 A1 | 9/2003 |
| WO | 2004/093981 A1 | 11/2004 |

OTHER PUBLICATIONS

Tass, Peter A., "Phase Resetting in Medicine and Biology: Stochastic Modelling and Data Analysis", pp. 1-13, 2007.

Tass, Peter, et al., "Detection of n:m Phase Locking from Noisy Data: Application to Magnetoencephalography", Oct. 12, 1998.

Office Action issued by the German Patent Office on Oct. 24, 2005 in the related German patent application.

* cited by examiner

METHOD AND DEVICE FOR DESYNCHRONIZING NEURAL BRAIN ACTIVITY, CONTROLLER AND METHOD FOR TREATING NEURAL AND/OR PSYCHIATRIC DISORDERS

This is a continuing application, filed under 35 U.S.C. §111(a), of International Application PCT/DE2005/002192, it being further noted that foreign priority benefit is based upon German Application No. 10 2004 060514.9 filed Dec. 16, 2004, the contents of the foregoing being incorporated herein by reference.

The invention relates to a method for desynchronizing neural brain activity, and to a device suitable therefor and a controller.

In the case of patients with neurological or psychiatric disorders such as, for example, Parkinson's disease, essential tremor, dystonia or compulsive disorders, nerve cell groups in circumscribed regions of the brain, e.g. the thalamus and the basal ganglia, are morbidly active, for example excessively synchronous. In this case, a large number of neurons form synchronous action potentials, that is to say that the neurons involved fire excessively synchronously. In a healthy patient, the neurons in these brain regions fire qualitatively differently, for example in an uncorrelated manner.

In the case of Parkinson's disease, the pathologically synchronous activity alters the neural activity in areas of the cerebral cortex, such as, for example, in the primary motor cortex, for example by imposing its rhythm on said areas, so that, finally, the muscles controlled by said areas develop pathological activity, e.g. a rhythmic tremor.

The object of the present invention is to provide a method and a device which can be used to treat patients without an adaptation to an unphysiological continuous stimulus taking place, and in which protracted calibration is not necessary, to be precise not even when the principal-frequency component of the pathologically rhythmic activity is subject to major fluctuations. Side effects are intended to be reduced or even prevented. Furthermore, the necessity of a hard phase reset is intended to be obviated, that is to say that the charge input is intended to be minimized. Furthermore, the effectiveness of the method is intended to be improved such that even patients with very serious clinical symptoms can be treated successfully.

The object is achieved according to the invention by means of the features specified in the independent claims.

The method and device according to the invention now make it possible to alleviate or completely suppress the patient's symptoms. Even patients with very serious clinical symptoms can be treated successfully. It is even possible to obtain curative effects, that is to say that the symptoms are not only simply suppressed under stimulation, but a cure takes place in the neurons, so that stimulated tissue unlearns the morbid tendency toward synchronous activity.

The drawings show a device suitable for carrying out the method.

In the figures:

FIG. 2b shows local field potential of the stimulated neuron populations that is associated with FIG. 2a FIG. 3 shows a multicontact electrode The device in accordance with FIG. 1 comprises an isolation amplifier 1, to which are connected at least one electrode 2 and also sensors 3 for detecting physiological measurement signals. In the case where one electrode 2 is present, this electrode comprises at least two contact points which can output stimuli. When there is more than one electrode present, at least two electrodes must each have at least one contact point which can output electrical stimuli. The isolation amplifier is furthermore connected to a unit 4 for signal processing and control, which is connected to an optical transmitter for the stimulation 5. The optical transmitter 5 is connected via optical waveguides 6 to an optical receiver 7, which is connected to a stimulator unit 8 for signal generation. The stimulator unit 8 for signal generation is connected to at least one electrode 2. A relay 9 or transistor is situated at the input region of the electrodes 2 into the isolation amplifier 1. The unit 4 is connected via a line 10 to a telemetry transmitter 11, which is connected to a telemetry receiver 12, which is situated outside the apparatus to be implanted and to which is connected a means for visualization, processing and storage of the data 13.

Figure 2A:
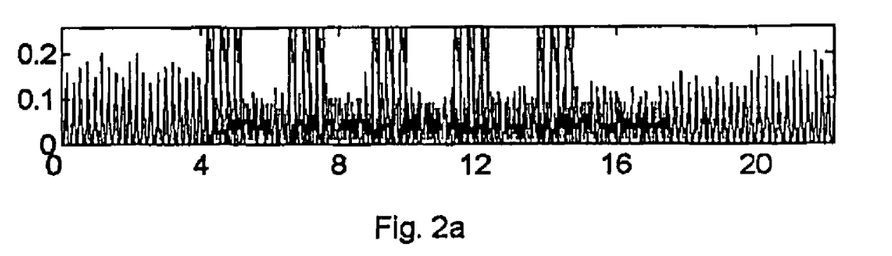
FIG. 2a shows neural firing patterns upon stimulation with five successions of sequences via three stimulation contacts

FIG. 2a shows the summation action potential of a morbidly active neuron population, that is to say the relative number of the action potentials produced by the neurons (that is to say the number of action potentials produced by the neurons divided by the number of all the neurons in the entire neuron population), before, during and after a stimulation. The latter comprises five identical orders of sequences separated by four pauses of equal length. Each order of sequences comprises a low-frequency succession of three sequences. The beginning and the end of a sequence are in each case indicated by a vertical line. Each sequence has the same configuration, that is to say that a high-frequency pulse train is in each case applied sequentially via in each three contact points each time in the same order, separated from one another by short pauses. The same high-frequency pulse train is in each case used for the three contact points. The pauses between the three high-frequency pulse trains of a sequence correspond approximately to one third of the average period of the neural activity to be desynchronized. The abscissa is the time axis in seconds, and the ordinate is dimensionless.

Figure 2B:
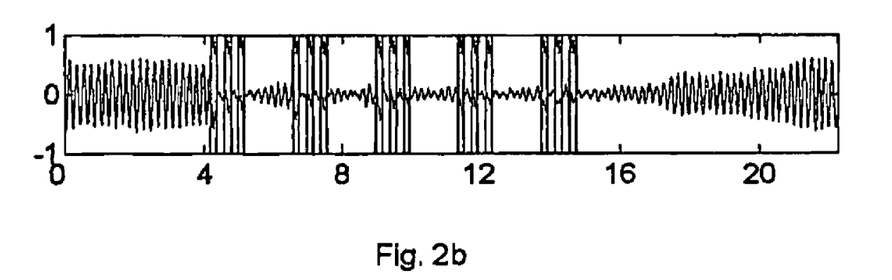

FIG. 2b shows the local field potential—associated with the stimulation process shown in FIG. 2a—of the stimulated morbidly active neuron population. The abscissa is the time axis in seconds, and the ordinate shows the local field potential in arbitrary units normalized to the maximum.

FIG. 3 shows a multicontact electrode 2 having the contact points 14.

Figure 1:
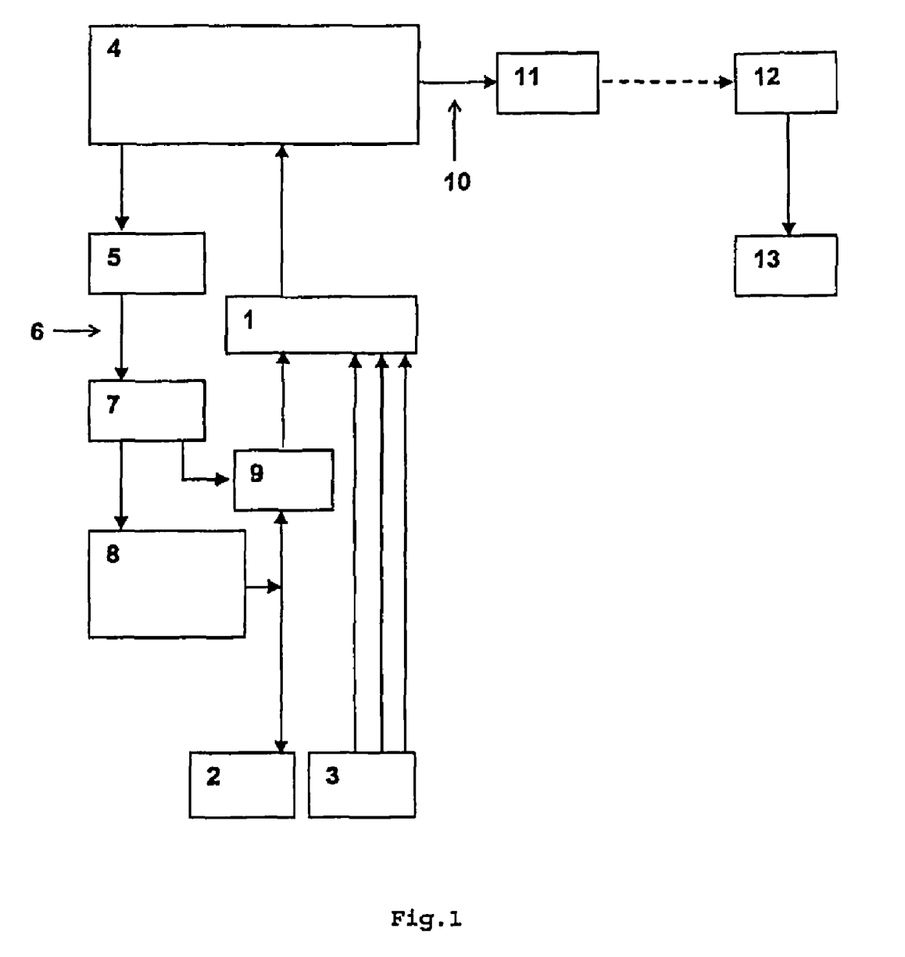
FIG. 1 shows a device according to the invention

By way of example, epicortical electrodes, deep electrodes, brain electrodes or peripheral electrodes may be used as sensors 3.

The electrode 2 comprises at least two wires, to the ends of which a potential difference is applied for stimulation purposes. The ends to which a potential difference is applied constitute contact points 14 which make contact with the tissue to be stimulated in order to stimulate it with electrical stimuli. They are referred to hereinafter as contact points 14. An electrode can have at least one contact point 14. The invention makes reference to contact points 14 hereinafter. In this case, the number of contact points 14 is not necessarily intended to match the number of electrodes, rather n+m contact points 14 can be distributed over n electrodes. In this case, m is preferably greater than n. The electrode 2 is a means for stimulus application.

In the broader sense it may also be a means for measuring physiological signals. In principle, the same contact points 14 used for stimulation can be used for measuring the physiological signals.

Therefore, the expression contact point 14, which experts refer to as "stimulation site", hereinafter denotes a tissue-side wire surface that is suitable for applying an electrical stimulus and/or measuring a physiological signal. Macro-electrodes or micro-electrodes may be involved in this case.

In addition, but not necessarily, a potential difference can be measured by means of the electrode 2 in order to detect pathological activity.

In a further embodiment, the electrode 2 may also comprise only an individual wire. In this case, for stimulation purposes, a potential difference is applied between the end of said wire, on the one hand, and a metallic counterpart, on the other hand. The metallic counterpart may be for example a housing of the device or a part thereof or any other arbitrary electrode or any other metallic object which is connected to the stimulator unit 8 analogously like the wire of the electrode 2.

In a further embodiment, electrode 2 may also comprise more than two individual wires that can be used both for determining a measurement signal in the brain and for the stimulation. By way of example, four wires may be accommodated in a conductor cable, in which case a potential difference can be applied or measured between different ends. The size of the derived or stimulated target region can thereby be varied. The number of wires from which the electrode is constructed is limited toward upper values only by the associated thickness of the cable to be inserted into the brain, so that as little brain material as possible is to be damaged. Commercially available electrodes comprise four wires, but the electrodes may also comprise five, six or more wires, but also only three wires.

In a preferred embodiment, at least two electrodes 2 can be structurally combined. For this purpose, by way of example, n wires with different contact points 14 to the brain can be combined in one brain electrode. The contact points 14 can essentially be arranged one above another and/or in a manner shifted radially with respect to one another.

The suitable electrodes are known to the person skilled in the art and are not restricted to the electrodes presented by way of example. The term electrode is also intended to encompass a chip having contact points 14.

For the case where the electrode 2 comprises more than two wires, at least two of said wires may also function as a sensor 3, so that this specific case gives rise to an embodiment in which the electrode 2 and the sensor 3 are combined in a single component.

The wires of the electrode 2 may have different lengths, so that they can penetrate to different brain depths. If the electrode 2 comprises n wires, then a stimulation can be carried out via at least one pair of wires, any subcombination of wires being possible when forming pairs. Sensors 3 which are not structurally combined with electrode 2 may additionally be present alongside this component.

The unit for signal processing and control 4 comprises means for univariate and/or bivariate and/or multivariate data processing as described for example in "Detection of n:m Phase Locking from Noisy Data: Application to Magnetoencephalography" by P. Tass, et al. in Physical Review Letters, 81, 3291 (1998).

The device is preferably equipped with means which identify the signals of the electrode 2 and/or of the sensors 3 as pathological and, in the case where a pathological pattern is present, output via the electrode 2 stimuli which cause the pathological neural activity either to be suppressed for a short time or to be modified in such a way that it comes closer to the natural, physiological activity. The pathological activity differs from the healthy activity by a characteristic change in its pattern and/or its amplitude, which are known to the person skilled in the art and which can be detected by known methods.

The means for identifying the pathological pattern are in this case a computer which processes the measured signals of the electrode 2 and/or of the sensor 3 and compares them with data stored in the computer. The computer has a data carrier which stores data determined in the context of a calibration procedure. By way of example, said data can be determined by the stimulation parameters being systematically varied in a series of test stimuli and the success of the stimulation via the electrode 2 and/or the sensor 3 being determined by means of the control unit 4. The determination can be effected by univariate and/or bivariate and/or multivariate data analysis for characterizing the frequency properties and the interaction (e.g. coherence, phase synchronization, directionality and stimulus-response relationship), as disclosed for example in P. A. Tass: "Phase resetting in Medicine and Biology. Stochastic Modelling and Data Analysis." Springer Verlag, Berlin 1999.

The device according to the invention therefore preferably comprises a computer which comprises a data carrier which carries the data of the clinical symptoms, compares them with the measurement data and, in the case where pathological activity occurs, outputs a stimulus signal to the electrode 2, with the result that the brain tissue is stimulated. The data of the clinical symptoms stored in the data carrier can be either person-specific optimum stimulation parameters determined by calibration, or a data pattern which has been determined from a patient collective and represents optimum stimulation parameters that typically occur. The computer identifies the pathological pattern and/or the pathological amplitude.

The control unit 4 may comprise for example a chip or some other electronic device having comparable computation power.

The control unit 4 preferably drives the electrode 2 in the following manner. The control data are forwarded from the control unit 4 to an optical transmitter for the stimulation 5, which drives the optical receiver 7 via the optical waveguide 6. Optical injection of control signals into the optical receiver 7 provides DC isolation between the stimulation controller and the electrode 2. This means that this prevents interference signals from the unit for signal processing and control 4 from being injected into the electrode 2. By way of example, a photocell may be used as the optical receiver 7. The optical receiver 7 forwards to the stimulator unit 8 the signals input via the optical transmitter for the stimulation 5. By means of the stimulator unit 8, targeted stimuli are then forwarded via the electrode 2 to the target region in the brain. For the case where measurement is also effected by means of the electrode 2, a relay 9 is also driven proceeding from the optical transmitter for the stimulation 5 via the optical receiver 7, which prevents the injection of interference signals. The relay 9 or the transistor ensures that the neural activity can be measured again directly after each stimulus, without overdriving the isolation amplifier. The DC isolation need not necessarily be effected by optical injection of the control signals, rather other alternative control processes can also be used. These may be for example acoustic inputs, for example in the ultrasonic range. Interference-free control can also be realized for example with the aid of suitable analog or digital filters.

In a further embodiment, the device according to the invention is preferably connected to means for visualization and processing of the signals and for data backup 13 via the telemetry receiver 12. In this case, the unit 13 may comprise the abovementioned methods for univariate and/or bivariate and/or multivariate data analysis.

In a further embodiment, the device according to the invention may be connected to an additional reference database via the telemetry receiver 13 in order for example to accelerate the calibration process.

The functioning of the device according to the invention and also the method according to the invention will be discussed below.

The description of the functioning of the device implicitly describes a device and a controller and also a method for treating illnesses which work according to the specified manner of functioning.

According to the invention, low-frequency sequences of high-frequency pulse trains, preferably short high-frequency pulse trains, which comprise individual pulses, are applied to the cerebral neurons via at least two contact points 14.

A low-frequency sequence of high-frequency pulse trains should be understood within the meaning of the invention to be an essentially periodic succession of high-frequency pulse trains having a frequency of 0.1 Hz to 50 Hz, preferably 1 Hz to 10 Hz, particularly preferably 2 Hz to 8 Hz.

The possible features of the individual pulses will be described below:

The individual pulses can have a duration of 0 to 10 µs, or 0 to 50 µs, 0 to 100 µs, 0 to 200 µs or—less preferably—up to 3000 µs.

An electrical individual pulse is understood to mean an essentially charge-neutral individual electrical pulse which is known to the person skilled in the art.

Charge-neutral within the meaning of the invention signifies that the time integral of the charge input is essentially zero.

The preferred amplitude of the individual pulses lies within the range of 0 to 16 V, preferably between 2 and 6 V.

The amplitude of an individual pulse is understood to mean the maximum of the magnitude of the time response of the charge input of said individual pulse.

The possible features of a high-frequency pulse train are explained below:

A short high-frequency pulse train within the meaning of the invention is understood to mean a short high-frequency succession of electrical individual pulses.

In a high-frequency pulse train, the duration of the individual pulses is only limited by the temporal distance to the subsequent individual pulse within the same high-frequency pulse train.

At a frequency of the high-frequency pulse train of e.g. 130 Hz, the period of the high-frequency pulse train of approximately 7.69 ms thus results as basic upper limit of the length of an individual pulse.

Short means that this high-frequency succession comprises at least two, preferably 3, 4, 5, 6, 7, 8, 9, 10, 11, 12, 13, 14, 15, 16, 17, 18, 19, 20, 50 or up to 100 individual pulses.

Preferably, the number of individual pulses which a short high-frequency pulse train comprises lies within the range of 3 to 15 individual pulses.

The basic upper limit of the number of individual pulses in a high-frequency pulse train is determined by the period duration of the periodic low-frequency succession with which the high-frequency pulse trains are applied.

If the frequency of the low-frequency succession of high-frequency pulse trains is 5 Hz, for example, then the duration of an individual high-frequency pulse train cannot exceed 200 ms. Given a frequency of 100 Hz of the high-frequency pulse train and a duration of 100 µs, the individual high-frequency pulse train can contain, in principle, a maximum of 20 individual pulses.

Since the effect of a high-frequency pulse train depends on the phase of a stimulated neural rhythm, the length of the high-frequency pulse train—in order to be able to modulate the phase dynamic range effectively—should essentially be at most ¾ of the period of the low-frequency succession and e.g. essentially preferably 1/10-¼ of said period.

Within the meaning of the invention, high-frequency signifies that the frequency preferably lies between 50 and 250 Hz, preferably between 80 and 150 Hz, particularly preferably between 100 and 140 Hz.

In a less preferred embodiment, it is also possible to use charge-neutral short high-frequency pulse trains which comprise different non-charge-neutral individual pulses.

The form of the individual pulses, that is to say the temporal profile of the charge input, can be symmetrical or asymmetrical in this case. That is to say that, in the case of these biphasic individual pulses, the cathodic anodic part of the individual pulse can be symmetrical or asymmetrical. In the symmetrical case, the cathodic part and the anodic part of the individual pulse are identical apart from the sign of the current flow. Besides biphasic individual pulses it is also possible to apply triphasic and multiphasic individual pulses.

Preferably, the form of the individual pulses is identical for all the individual pulses of a high-frequency pulse train, but it can also be different for at least two individual pulses within a high-frequency pulse train.

Preferably, the amplitude is identical for all the individual pulses, but it can also be different for at least two individual pulses within a high-frequency pulse train.

Preferably, the duration is identical for all the individual pulses, but it can also be different for at least two individual pulses within a high-frequency pulse train.

The amplitude of the high-frequency pulse trains can be of an order of magnitude of 0 to 16 V. Preferably, the amplitude of the high-frequency pulse trains lies between 2 and 7 V. The customary resistance of electrode and brain tissue lies for example within the range of 800 to 1200 O.

The frequency of a high-frequency pulse train comprising identical individual pulses is the rate at which the individual pulses are applied. In other words, the period of a high-frequency pulse train is the time interval between the beginning of successive individual pulses. If the high-frequency pulse train contains at least two individual pulses which differ with regard to their form and/or duration, the period of the high-frequency pulse train is understood to be the time interval between the marker events of successive individual pulses. A marker event is understood to be a characteristic feature to be employed, such as, for example, beginning of an individual pulse, end of an individual pulse, in the case of biphasic or multiphasic individual pulses beginning or end of a specific phase of an individual pulse, instant of the maximum amplitude, instant of the centroid of the magnitude of the time response of the charge input, n-th maximum or n-th minimum or n-th point of inflection of the time response of the charge input, where n is a positive integer.

The period does not have to be constant within a high-frequency pulse train. Rather, at least two of the periods within a high-frequency pulse train can be different. In other words, the instantaneous frequency—referring to the individual period—of a high-frequency pulse train can vary within a high-frequency pulse train. The order of the individual periods in a high-frequency pulse train can be provided by deterministic algorithms and/or stochastic algorithms and/or combinations of the two.

A high-frequency pulse train can also comprise individual pulses of which at least two individual pulses have different forms and/or different amplitudes and/or different durations.

The form and/or the duration and/or the amplitude of the individual pulses can be provided by deterministic and/or stochastic algorithms and/or combinations of the two. A combination of stochastic and deterministic algorithms involves a functional relationship in which deterministic and stochastic terms are combined with one another functionally, e.g. by addition or multiplication. By way of example, the amplitude of the j-th individual pulse may be given by f(j), where f is a deterministic function and/or a stochastic process and/or a combination of the two.

Possibilities of the high-frequency pulse trains applied via an individual stimulation contact within the low-frequency succession of high-frequency pulse trains will be described below:

A low-frequency succession of short high-frequency pulse trains comprises preferably 2-100, particularly preferably 2-20 or 2-10 high-frequency pulse trains.

The low-frequency succession of short high-frequency pulse trains preferably comprises a periodic succession of short high-frequency pulse trains whose frequency essentially corresponds to the pathological frequency—for example approximately 5 Hz in the case of Parkinson's disease—or a small integral multiple, e.g. double, triple or quadruple the frequency.

The period of the low-frequency succession of short high-frequency pulse trains is referred to hereinafter as stimulation period. Low-frequency within the meaning of the invention should be understood to be frequencies of 0.5-50 Hz, preferably 2-20 Hz, particularly preferably 2-10 Hz.

A low-frequency succession of short high-frequency pulse trains preferably comprises the same high-frequency pulse trains. However, at least two high-frequency pulse trains of such a low-frequency succession can also differ with regard to their pattern.

The pattern of a high-frequency pulse train comprises the following properties:
A) the number of individual pulses,
B) the form of the individual pulses,
C) the durations of each of the individual pulses,
D) the amplitudes of each of the individual pulses,
E) the periods between each of the individual pulses.

Within a low-frequency succession of short high-frequency pulse trains, the pattern can be varied from high-frequency pulse train to high-frequency pulse train in deterministic fashion and/or in stochastic fashion and/or in combined deterministic-stochastic fashion. In particular, within a low-frequency succession of short high-frequency pulse trains, the frequency of at least two short high-frequency pulse trains can be different.

Preferably, all the high-frequency pulse trains of a low-frequency sequence of high-frequency pulse trains have the same number of individual pulses. However, it is also possible for at least two high-frequency pulse trains to comprise a different number of individual pulses.

Preferably, all the high-frequency pulse trains of a low-frequency sequence of high-frequency pulse trains have the same frequency. However, it is also possible for at least two high-frequency pulse trains to comprise individual pulses having different frequencies.

Preferably, the amplitude of the individual pulses is identical for all the high-frequency pulse trains of a low-frequency sequence of high-frequency pulse trains, but it can also be different for at least two high-frequency pulse trains.

Temporal Structure of the Low-Frequency Succession of High-Frequency Pulse Trains:

The low-frequency succession of high-frequency pulse trains need not be strictly periodic. Within a low-frequency succession of high-frequency pulse trains, the time interval between successive high-frequency pulse trains can be varied in deterministic fashion and/or in stochastic fashion and/or in deterministic-stochastic fashion.

Within a low-frequency succession of HF pulse trains, the time interval between successive high-frequency pulse trains and/or the pattern of the respective high-frequency pulse train can be varied in deterministic fashion and/or in stochastic fashion and/or in combined deterministic-stochastic fashion.

In this case, the controller of the device according to the invention can regulate the low-frequency succession of HF pulse trains in the following manner:

The pattern of the j-th high-frequency pulse train is designated by $H_j$.

The pause after the j-th high-frequency pulse train is designated by $p_j$.

A low-frequency succession of high-frequency pulse trains which comprises e.g. 4 high-frequency pulse trains accordingly has the following structure:

$$H_1 p_j H_2 p_2 H_3 p_3 H_4 p_4$$

The controller of the device according to the invention can determine the patterns $H_j$ (j=1, 2, ...) and the pauses $p_j$ (j=1, 2 ...) in accordance with a deterministic and/or stochastic and/or combined deterministic-stochastic algorithm.

In this case, $H_j$ is the following vector:

$$H_j = (m_j, \underline{P}_{jk}, \underline{Z}_{j1}, \underline{Z}_{j2}, \ldots \underline{Z}_{jm}),$$

with underscore () as the symbol for a vector,
$m_j$=number of individual pulses in the j-th high-frequency pulse train,
$\underline{P}_{jk}$=duration of the pause after the k-th individual pulse in the j-th high-frequency pulse train,
$\underline{Z}_{jk}$=vector which determines the properties $\underline{Z}_{jk}=(\underline{Z}_{jk}^{(1)}, \underline{Z}_{jk}^{(2)}, \ldots \underline{Z}_{jk}^{(m)})$ of the k-th individual pulse in the j-th high-frequency pulse train.

In the most general case, $\underline{Z}_{jk}$ is the time response of the k-th individual pulse in the j-th high-frequency pulse train. In this case, the length of the vector is determined by the sampling rate.

The stock of possible forms of the individual pulses is preferably limited, so that the form can be unambiguously characterized with significantly fewer parameters, which leads to simpler control. If e.g. only biphasic, rectangular individual pulses are used, then $\underline{Z}_{jk}$ comprises only six components:
1. beginning of the individual pulse, e.g. $\underline{Z}_{jk}^{(1)}$=0 μs
2. end of the individual pulse, e.g. $\underline{Z}_{jk}^{(2)}$=500 μs
3. binary information items code whether the first phase of the individual pulse is cathodic, and the second anodic ($\underline{Z}_{jk}^{(3)}$=1), or the first phase of the individual pulse is anodic and the second phase cathodic ($\underline{Z}_{jk}^{(3)}$=0),
4. duration of the first phase (e.g. $\underline{Z}_{jk}^{(4)}$=100 μs)
5. amplitude of the first phase (e.g. $\underline{Z}_{jk}^{(5)}$=4 V),
6. amplitude of the second phase (e.g. $\underline{Z}_{jk}^{(6)}$=1 V).

According to the invention, the low-frequency successions of short high-frequency pulse trains are applied via at least two contact points 14 situated on at least one electrode 2.

In this case, according to the invention, the short high-frequency pulse trains are applied via n electrodes or contact points 14 with a temporal shift of the individual high-frequency pulse trains of essentially T/n, where T is the period of the low-frequency succession of high-frequency pulse trains. The deviation from T/n may in this case amount to ±0.25 T or more, up to ±0.75 T, without the effect according to the invention being lost.

Preferably, with 2, 3, 4, 5 or 6 electrodes 2 or contact points 14, the respective high-frequency pulse trains are applied with a temporal shift of T/2, T/3, T/4, T/5 or T/6.

By way of example, in the case of three electrodes 2 each having a contact point 14 or contact points 14, firstly at time t=0s a high-frequency pulse train is applied via electrode number one or contact point 14 (No. 1), at time t=T/3 a high-frequency pulse train is administered via electrode number two or contact point 14 (No. 2), and at time t=2 T/3, finally, a high-frequency pulse train is applied via electrode number three or contact point 14 (No. 3). However, any other possible sequence can also be used for driving the individual electrodes or the contact points 14. That is to say that 1-3-2, 2-1-3, 2-3-1, 3-1-2 and 3-2-1 would also be possible orders instead of the order 1-2-3 chosen by way of example.

If, given n high-frequency pulse trains which are applied sequentially, a pair of high-frequency pulse trains is applied with a temporal shift of approximately half a period, then the following can alternatively be effected:

1. The high-frequency pulse train applied first is applied unchanged. The high-frequency pulse train delayed by essentially half a period is applied without a time delay but with reversal of the polarity.
2. The later high-frequency pulse train is applied unchanged. The earlier high-frequency pulse train is applied with a temporal delay of approximately essentially half a period but with polarity reversal.

According to the invention, the target population is understood to mean the nerve cell population stimulated directly by an implanted electrode.

A target population is stimulated directly by an electrode which is implanted in it or close to it. The nerve cell population which is morbidly synchronously active is referred to as the area to be desynchronized or as the nerve cell population to be desynchronized or as the neuron population to be desynchronized. The latter is not tied to anatomical boundaries. Rather, it can also be understood to mean at least one component comprising the group at least one part of at least one anatomical area, at least one complete anatomical area.

The area to be desynchronized can be stimulated either directly or indirectly.

Direct stimulation via a stimulation electrode 2:

In this case, the stimulation electrode 2 is situated in the area to be desynchronized. In this case, said electrode 2 influences the target population situated in the area to be desynchronized.

Indirect stimulation via a stimulation electrode 2:

In this case, the area to be desynchronized is not stimulated directly by means of electrode 2. Rather, a target population or a fiber bundle which is functionally closely linked to the area to be desynchronized is stimulated via the stimulation electrode 2. In this case, the stimulation effect is propagated to the area to be desynchronized preferably via anatomical links. For indirect stimulation, the term target area will be introduced as a generic term for target population and fiber bundle. The term target area shall be understood hereinafter as the neuron population which is functionally closely linked to the area to be desynchronized, and the connecting fiber bundle.

The duration between the beginning of the stimulus application via the j-th electrode 2 or contact point 14 and the first maximum of the stimulus response or the magnitude of the stimulus response, $t_j^{(k)}$, is determined for each individual stimulus application. In $t_j^{(k)}$, the index j stands for the j-th electrode 2 or contact point 14, while the index k stands for the k-th applied stimulus. The average duration between stimulus beginning and stimulus response is then determined separately from this for each stimulation electrode 2 or contact point 14 via which indirect stimulation is effected, according to the following formula 1:

$$\bar{\tau}_j = \frac{1}{L_j} \sum_{k=1}^{L_j} \tau_j^{(k)}. \quad \text{Formula 1}$$

In this case, $L_j$ is the number of stimuli applied via the j-th stimulation electrode 2 or contact point 14. $L_j$ can, but need not, be identical for all the stimulation electrodes 2 or contact points 14 via which indirect stimulation is effected.

For the desynchronizing stimulation, the conduction time $\bar{\tau}_j$ determined in this way is taken into account in the following way:

If, in the case of direct stimulation of the neuron population to be desynchronized, a stimulus were applied at time t via the j-th stimulation electrode 2 or contact point 14, then in the case of indirect stimulation, that is to say in the case of a stimulation which is not effected directly in the neuron population to be desynchronized, but rather in a fiber bundle linked thereto and/or a neuron population linked thereto, the stimulus is administered at time $t-\bar{\tau}_j$ via the j-th stimulation electrode 2 or contact point 14.

In one embodiment, the order of the electrodes or the contact points 14 during the stimulus application can remain the same, that is to say that the different electrodes or contact points 14 always apply the stimuli according to the invention in a specific predetermined order that can be chosen freely.

In a particularly preferred embodiment, within a low-frequency succession of high-frequency pulse trains that is administered via a plurality of electrodes 2 or contact points 14, the order of the stimulus application via the different electrodes/contact points 14 is varied in deterministic fashion and/or in stochastic fashion and/or in combined deterministic-stochastic fashion.

The structure of a low-frequency succession of sequences:

The succession of the individual high-frequency pulse trains applied in time-delayed fashion via n electrodes 2 or contact points 14 is referred to as sequence of high-frequency pulse trains.

Temporal driving of the sequences:

The device according to the invention can drive the instants of successive sequences in such a way that the latter are applied strictly periodically. A low-frequency succession of sequences is involved in this case. If at least two of said sequences in this case have a different order of electrode driving, then not all of the low-frequency successions of high-frequency pulse trains that are administered via the n electrodes 2 or contact points 14 can have the same period as the low-frequency succession of the sequences.

The time intervals between successive sequences can be chosen in deterministic fashion and/or in stochastic fashion and/or in combined deterministic-stochastic fashion.

Selection of the m electrodes of a total of n electrodes or contact points via which stimulation is effected in a specific sequence; $m \leq n$:

It is possible, even in the case of one sequence, to drive only $m \geq 2$ of the total of n ($m \leq n$) electrodes 2 or contact points 14 with a time delay of preferably T/m. The configuration of a sequence is understood to be (i) the selection of the $m \geq 2$ electrodes 2 or contact points 14 from the total n ($m \leq n$) electrodes or contact points 14 and (ii) the order thereof during driving.

By way of example, the configuration of a sequence given a total of n=4 electrodes 2 or contact points 14 may be 2-3-1, that is to say that only the electrodes 2 or contact points 14 1, 2 and 3 are driven, to be precise in the order 2-3-1.

The configuration can be varied within an order of sequences in deterministic fashion and/or in stochastic fashion and/or in combined deterministic-stochastic fashion.

Overall, within an order of sequences, the configurations thereof, the time intervals between successive sequences and the patterns of the high-frequency pulse trains used in the respective sequences can be coordinated with one another and varied in deterministic fashion and/or in stochastic fashion and/or in combined deterministic-stochastic fashion.

The structure of the applied sequences is therefore of the form $$S_1P_1S_2P_2S_3P_3\ldots S_kP_k.$$

$S_j$ designates the number and the type including configuration and pattern of the HF pulse trains used in the sequences used in the j-th order of sequences. $P_j$ designates the duration of the subsequent pause.

In one possible, but not preferred embodiment of the device according to the invention, the succession $$S_1P_1S_2P_2S_3P_3\ldots S_kP_k$$

is determined without demand control, that is to say without feedback, in stochastic fashion and/or in deterministic fashion and/or in combined deterministic-stochastic fashion. In the very simplest case, $S_1\,P_1\,S_2\,P_2\,\ldots$ is a strictly periodic succession $S_1\,P_1\,S_1\,P_1\,\ldots$.

In one preferred embodiment, the device according to the invention has a demand control. For this purpose, the neural activity is measured by means of at least one of the stimulation electrodes and/or at least one additional electrode 2 or contact point 14 (sensor 3), and processed by means of univariate and/or bivariate and/or multivariate data analysis methods.

Depending on the results thus obtained, the succession $S_1\,P_1\,S_2\,P_2\,\ldots$ is modified in such a way that a desynchronization that is as efficient as possible is obtained with as little stimulation current as possible.

There are a number of possibilities in this case:

(i) Demand-controlled timing:

The sequence orders $S_1$, $S_2$, $S_3$, etc. are not regulated, i.e. modified depending on the feedback signal and/or on the feedback signals. Preferably exclusively the duration of the pauses $P_1$, $P_2$, $P_3$, ... etc. is regulated in demand-controlled fashion, that is to say that whenever a threshold value of the pathological feature is detected, the pause $P_k$ is ended and the succeeding sequence order $S_{k+1}$ is applied. The simplest case involves always applying the same sequence order $S_1$ in demand-controlled fashion with different pauses:

$$S_1P_1S_1P_2S_1P_3S_1P_4\ldots.$$

(ii) Demand-controlled variation of the sequence order $S_1$, $S_2$, $S_3$ etc. without regulation of the pauses $P_1$, $P_2$, $P_3$ etc.:

The manifestation of the pathological feature is measured during the pauses $P_1$, $P_2$, $P_3$ etc. The respectively subsequent sequence order $S_k$ or the respectively subsequent sequence orders $S_K$, $S_{k+1}$, $S_{k+2}$, ..., $S_{k+q}$ are regulated depending on this, where q is a positive integer.

In a simple embodiment, the manifestation of the pathological feature is measured during constant pauses in each case and the amplitude of the high-frequency pulse trains of the succeeding sequence order $S_k$ is regulated depending on this. Let $X_{k-1}$ be the variable which describes the manifestation of the pathological feature during the pause $P_{k-1}$; it is then possible, in a simple embodiment, to regulate for example the amplitude $A_k$ of all the high-frequency pulse trains of the sequence order $S_k$ depending on $X_{k-1}$.

In this application, the expression "$A_k$ is regulated depending on $X_{k-1}$" is understood to mean the following. $A_k$ is regulated depending on $X_{k-1}$ by methods of regulation technology which are known to the person skilled in the art. By way of example $A_k$ is determined in accordance with $A_k=F(X_{k-})$, where F is a function which is piecewise linear or nonlinear and $A_k$ is always limited upward, i.e. toward maximally values of e.g. 5V, in order to prevent an excessively strong stimulation.

This exemplary embodiment results in the succession $$S_1P_1S_2P_1S_3P_1S_4P_1\ldots,$$

where the same pause $P_1$ is in each case inserted between the sequence orders $S_1$, $S_2$, $S_3$, ... etc. The sequence orders $S_1$, $S_2$, $S_3$ ... differ only with regard to the amplitude $A_k$ of their high-frequency pulse trains.

In a further, alternative simple embodiment, the demand control of the sequence orders $S_1$, $S_2$, $S_3$ etc. is carried out in such a way that, rather than the amplitude of the high-frequency pulse trains of the sequence order $S_1$, $S_2$, $S_3$ etc., the length of the sequence orders $S_1$, $S_2$, $S_3$ etc. is regulated depending on the manifestation of the pathological feature $X_k$. By way of example, in a simple embodiment, there may be a "master sequence order" $S_M$ comprising a succession of sequences $Seq_1$, $Seq_2$ etc. with interposed pauses $Pa_1$, $Pa_2$ etc., to be precise of the form $S_M=Seq_1$, $Pa_1$, $Seq_2$, $Pa_2$, $Seq_3$, $Pa_3$, ... etc.

The length L of $S_M$ is regulated depending on the manifestation of the pathological feature $X_k$, where $S_M$ of length L denotes:

$$S_M=Seq_1, Pa_1, Seq_2, Pa_2, Seq_3, Pa_3\,Seq_L.$$

In the simplest case, the sequences $Seq_1$, $Seq_2$, etc. are identical, such that $S_M$ of length L is a temporally equidistant succession of L individual sequences $Seq_i$.

(iii) Combined regulation, i.e. demand-controlled variation of the pauses $P_1$, $P_2$, etc. and demand-controlled variation of the sequence order $S_1$, $S_2$ etc.:

In a simple embodiment of the device according to the invention, e.g. the length $l_k$ of the high-frequency pulse trains in the sequence order $S_k$ is regulated depending on the manifestation of the pathological feature $X_{k-1}$ during the pause $P_{k-1}$.

In order to be able to apply the sequence orders $S_1$, $S_2$ etc. in an exemplary embodiment of strictly periodic offset (i.e. end point of the stimulation)—which is advantageous for rapid desynchronization—the lengths of the pauses $P_1$, $P_2$, etc. must be correspondingly varied compensationally. Long high-frequency pulse trains in $S_k$ lead to a lengthening of the sequence order $S_k$. In order that the offset of $S_k$, the end of the last high-frequency pulse train of $S_k$, can be effected in accordance with a strict periodicity, the preceding pause $P_{k-1}$ must be correspondingly shortened.

The following succession thus results: $S_1$, $P_1$, $S_2$, $P_2$, $S_3$, $P_3$, ..., where the $S_1$, $S_2$ etc. differ only with regard to the length of their high-frequency pulse trains and $P_{k-1}$ is in each case chosen such that the offset (i.e. the instant of the end)—or less preferably—the onset (i.e. the instant of the beginning) of $S_k$ is effected strictly periodically.

In a further embodiment of the device according to the invention, the length of the pauses $P_1$, $P_2$ etc. can additionally also be varied alongside the length of the high-frequency pulse trains.

In one exemplary embodiment of the device according to the invention, the above-explained regulation of the length $l_k$ of the high-frequency pulse trains of the sequence order $S_k$ is supplemented by lengthening the pause $P_{k-1}$ in the event of the manifestation $X_{k-1}$ falling below a specific threshold value $X_{min}$ of the pathological feature during the pause $P_{k-1}$.

The lengthening of the phase $P_{k-1}$ can be effected for example in quantized fashion. That is to say that $P_{k-1}$ is lengthened by a period T which typically corresponds to the period of the pathological neural activity or a small integral multiple thereof.

If, after the lengthening of $P_{k-1}$, the manifestation $X_{k-1}$ still falls below $X_{min}$, then $P_{k-1}$ is once again lengthened by T, etc., until $X_{k-1}$ finally exceeds $X_{min}$. The length of the high-frequency pulse trains in $S_k$ is then regulated depending on $X_{k-1}$ as described above.

For the demand control described above, the device according to the invention preferably has means which determine the manifestation of the pathological feature. For this purpose, the feedback signal representing the activity of the neuron population to be desynchronized is measured by means of sensor 3. Said feedback signal is forwarded to the unit 4 for signal processing and/or regulation, which functions as means for identifying a pathological feature. As soon as the unit 4 for signal processing and/or regulation identifies a pathological feature in the feedback signal, a stimulus is applied. A pathological feature should be understood to mean for example the following properties of the feedback signal:

a) The amplitude of the feedback signal exceeds a threshold value. In a preferred embodiment, therefore, the device according to the invention is equipped with means for identifying a threshold value of the feedback signal. In this case, preferably the feedback signal itself or its magnitude or its amplitude is compared with the threshold value. In this embodiment, the means for identifying the threshold value can be programmed in such a way that it compares for example the feedback signal itself and/or its magnitude and/or its amplitude with the threshold value. The amplitude is determined either in a simple version by means of determining the magnitude of the signal, or with bandpass filtering and subsequent Hilbert transformation or wavelet analysis. In this case, the unit 4 for signal processing and/or regulation is programmed in such a way that it can carry out a determination of the magnitude of the signal and/or a bandpass filtering with Hilbert transformation and/or a wavelet analysis. The feedback signal or its magnitude is particularly preferably used since the calculation of the amplitude signifies a significantly higher computational complexity, and the accuracy of this calculation depends on the correct number of algorithmic parameters. Moreover, the determination of the amplitude cannot be carried out on an individual measured value of the feedback signal, but rather has to be carried out in a sufficiently large time interval known to the person skilled in the art. This form of analysis of the feedback signal in a moving time window somewhat delays the identification of the pathological feature.

The form of the analysis of the form of the feedback signal as described under a) is to be applied if exclusively or predominantly the pathological activity to be desynchronized is measured by means of sensor 3.

b) If activity which is not yet illness-specific, for example from other neuron populations, is additionally measured by means of sensor 3 alongside said activity, a further algorithmic step must be introduced in the analysis of the feedback signal. Since the illness-specific activity typically occurs in a frequency range which is different from the frequency range of the non-illness-specific activity, it preferably suffices for this purpose to carry out an estimation of the activity in the illness-specific frequency range. The frequency of the illness-specific activity is determined for example by determining the temporal difference between successive trigger points. Trigger points are characteristic points such as maxima, minima, points of inflection and zero crossings. This analysis is preferably carried out in a moving time window, the mean value of a plurality of temporal differences being formed, whereby the stability of the frequency estimation is increased. As an alternative, the frequency estimation can also be determined by the spectral estimation methods and other frequency estimators which are known to the person skilled in the art. For this purpose, the device according to the invention in one particular embodiment has means for estimating the activity in the illness-specific frequency range, such as spectral estimation methods, wavelet analysis, etc. This is realized by a frequency analysis, for example, by means for carrying out a frequency analysis. By way of example, it is possible to determine the spectral energy in the illness-specific frequency range in a moving window. As an alternative, after bandpass filtering, the amplitude in the illness-specific frequency range can be determined by determining the maximum of the bandpass-filtered signal or by determining the mean value of the magnitude of the bandpass-filtered signal or with subsequent Hilbert transformation or by means of wavelet analysis. For this purpose, the device according to the invention has for example means for bandpass filtering of the amplitude and means for determining the maximum of the bandpass-filtered signal and/or means for determining the mean value of the magnitude of the bandpass-filtered signal and/or means for carrying out a Hilbert transformation and/or a wavelet analysis.

The device according to the invention can work with a threshold value criterion as described above. By way of example, the stimulation can be modified depending on the manifestation of a pathological feature. In particular, the stimulation can cease until the pathological feature exceeds a threshold value. In this embodiment, the exceeding of the threshold value signals the demand for a renewed stimulation.

Establishing the demand:

For at least two reasons, there is no unique relationship between the manifestation of the pathological feature and the manifestation of the illness-specific symptoms. On the one hand, the distance between sensor 3 and the area in which the feedback signal is generated governs the amplitude in the illness-specific frequency range. On the other hand, a specific manifestation of the illness-specific feature, that is to say the manifestation of the rhythmic activity in the illness-specific frequency range, is not unambiguously linked to the illness-specific symptoms. Since the illness-specific rhythm affects complex nerve networks in the brain which typically, on top of everything else, do not satisfy simple linear dynamic laws, no unambiguous relations hold true between the illness-specific rhythm and manifestation of the symptoms. If, for example, the illness-specific rhythm does not adequately match the biomechanically predetermined natural frequency of an extremity, the tremor caused by the illness-specific rhythm is significantly less than if the illness-specific rhythm resonantly matches the biomechanically predetermined natural frequency of the extremity.

In the case of a position of the sensor 3 that detects the feedback signal, the measured activity is in an empirical range which is known to the person skilled in the art. The value of the manifestation of the illness-specific feature of the feedback signal measured by means of sensor 3 is referred to as a threshold which, if exceeded, typically results in the occurrence of symptoms, for example of the tremor. The threshold is a parameter which must be chosen for the embodiment of the demand-controlled timing described in section 4.3. The device according to the invention therefore comprises means for identifying a threshold value. The method according to the invention of demand-controlled timing affords the advantage that the effectiveness of the device according to the invention does not critically depend on the choice of the threshold, rather there is a wide error tolerance with regard to the choice of the threshold, for example within a range of up to 50% of the maximum manifestation of the illness-specific feature. The threshold is chosen either intraoperatively or preferably in the initial days after the operation by measurement of the feedback signal by means of sensor 3, with determination of the manifestation of the illness-specific feature and comparison with the manifestation of the symptoms, for example the intensity of the tremor.

In a less preferred embodiment of the demand-controlled timing, a representative value, for example the mean value, of a collective of threshold values measured in patients is adopted as the threshold.

According to the invention, the target population is understood to mean the nerve cell population stimulated directly by an implanted electrode.

A target population is stimulated directly by an electrode which is implanted in it or close to it.

The nerve cell population which is morbidly synchronously active is referred to as the area to be desynchronized or as the nerve cell population to be desynchronized as the neuron population to be desynchronized. The latter is not tied to anatomical boundaries. Rather, it can also be understood to mean at least one component comprising the group at least one part of at least one anatomical area, at least one complete anatomical area.

The area to be desynchronized can be stimulated either directly or indirectly.

Direct stimulation via a stimulation electrode 2:

In this case, the stimulation electrode 2 is situated in the area to be desynchronized. In this case, said electrode 2 influences the target population situated in the area to be desynchronized.

Indirect stimulation via a stimulation electrode 2:

In this case, the area to be desynchronized is not stimulated directly by means of electrode 2. Rather, a target population or a fiber bundle which is functionally closely linked to the area to be desynchronized is stimulated via the stimulation electrode 2. In this case, the stimulation effect is propagated to the area to be desynchronized preferably via anatomical links. For indirect stimulation, the term target area will be introduced as a generic term for target population and fiber bundle. The term target area shall be understood hereinafter as the neuron population which is functionally closely linked to the area to be desynchronized, and the connecting fiber bundle.

The stimulation mechanism according to the invention involves stimulation within a period of the oscillatory activity in the neuron population to be desynchronized by means of the individual electrodes 2 at specific, typically different, instants. The periods of time between these individual stimuli are specified as fractions of the period of the oscillatory activity to be desynchronized and preferably amount essentially to an N-th of the period, where N is a small integer, for example 4. In this case, N is an integer, preferably below 1000, particularly preferably less than 100, in particular less than 10.

Embodiment for the case where all the electrodes or contact points 14 are positioned in the nerve cell population to be desynchronized:

The N electrodes or contact points 14 are preferably intended to be arranged in such a way that approximately an N-th of the nerve cell population to be desynchronized can be stimulated with each individual electrode or contact point 14. This can be realized with a different number of electrodes or contact points 14 and with a different geometrical arrangement of the electrodes or contact points 14 with respect to one another. It is possible for example to choose any desired asymmetrical arrangement. Essentially symmetrical arrangements are preferred, however, since they enable the stimulation-dictated functional division into subpopulations with the least current input. By way of example, the end points of the electrodes or the contact points 14, projected along the electrodes, may essentially produce a square. It is also possible for example to use six electrodes or contact points 14. In this case, four preferably arranged essentially in a square lie in one plane, while the other two lie essentially equidistantly perpendicular to said plane, their connecting line essentially forming the axis of rotation of the four electrodes arranged in a square. The electrodes or contact points 14 may at least in part have different lengths in order to realize different geometrical arrangements.

Embodiment for the case where at least one electrode 2 or contact point 14 is not positioned in the nerve cell population to be desynchronized:

This stimulation form involves stimulation in at least one target area, which is different from the area to be desynchronized. In this case, as described above, the indirect stimulation can be effected by stimulation of a neuron population that is different from the nerve cell population to be desynchronized, and/or by stimulation of a fiber bundle linked to the nerve cell population to be desynchronized. In this case, either at least one electrode 2 or contact point 14 or a multi-electrode or multi-contact-point 14 arrangement as described above can be used in a target area, or in the area to be desynchronized.

The mechanism of action of the stimulation techniques according to the invention outlined above is based on the fact that the time-offset stimulation of parts of the neuron population to be desynchronized results only in a phase shift of the collective oscillations in the respective subpopulations with respect to one another. In contrast to the prior art, that is to say in particular in contrast to the method described in the application DE 103 18 071, the stimulation techniques according to the invention make it possible for the first time to produce the phase shift between the collective oscillations in the respective subpopulations with minimal stimulus intensity, on the one hand, and in seriously affected patients, on the other hand. The morbid interaction between the neurons of the target population then has the effect that, as a reaction to the phase shift between the subpopulations, the entire target population transiently passes through a desynchronized state. This transient desynchronization occurring by virtue of the morbid interactions between the affected neurons as a consequence of the targeted stimulus action according to the invention is the effective principle of the device according to the invention. A repetitive application of stimuli leads to a repetitive desynchronization, so that a state of pronounced desynchronization is maintained in the target population by means of the above-described regulation according to the invention.

The success of the stimulation can be checked immediately even intraoperatively when the deep electrode is inserted. It is thereby possible to significantly improve the process of finding the suitable target point. For the previous demand-controlled methods, a calibration is required which lasts for longer than 30 minutes per electrode. This is not feasible intraoperatively and is not reasonable for the (not anesthetized) patient.

The new stimulation methods can also be applied to neurological and/or psychiatric disorders in which pathological rhythms have greatly fluctuating frequencies. In particular, intermittent rhythms (i.e. rhythms occurring for a short time) can also be desynchronized by means of the new methods. This means that the new stimulation methods can be applied to far more disorders, primarily also to epilepsy disorders.

With the device according to the invention, the following illnesses or symptoms can be treated by desynchronization of suitable brain areas by means of the new stimulation methods.

In all neurological and psychiatric disorders in which pathological neural synchronization plays a relevant part for the manifestation of the illness-specific symptoms, for example: Parkinson's disease, essential tremor, dystonia, compulsive disorders, tremor in the case of multiple sclerosis, tremor on account of a stroke or some other, for example tumorous, tissue damage, for example in the region of the thalamus and/or the basal ganglia, choreoathetosis and epilepsy, where the enumeration is not intended to be restrictive.

The following target areas are used in the standard method used at the present time, high-frequency continuous stimulation, by way of example:

In the case of Parkinson's disease the nucleus subthalamicus or the globus pallidum internum or in the case of tremor-dominant Parkinson's disease the thalamus, for example the nucleus ventralis intermedis thalami.

In the case of essential tremor the thalamus, for example the nucleus ventralis intermedius thalami.

In the case of dystonia and choreoathetosis the globus pallidum internum.

In the case of epilepsy the nucleus subthalamicus, the hippocampus, the substantia nigra, the cerebellum, thalamic core regions, for example the nucleus ventralis intermedius thalami, nuclei anteriores thalami, nucleus centromedianus thalami or nucleus caudatus.

In the case of tremor on account of multiple sclerosis the nucleus ventralis intermedius thalami.

In the case of compulsive disorders the capsula interna or the nucleus accumbens.

By way of example, the target areas enumerated above for the respective disorders can be chosen in the case of the device according to the invention. Since either no calibration is required or the calibration can be carried out very rapidly in the case of the device according to the invention, first makes it possible to thoroughly test, in the context of the electrode implantation, alternative target areas for which the desynchronizing effect of the device according to the invention can be developed even better.

The invention likewise encompasses a controller which controls the specified functioning of the device according to the invention, and also the use of the device and of the controller for the treatment of illnesses including Parkinson's disease, essential tremor, dystonia, compulsive disorders, choreoathetosis, tremor in the case of multiple sclerosis, tremor on account of a stroke or some other, for example tumorous, tissue damage, for example in the region of the thalamus and/or the basal ganglia, epilepsy and disfunctions after a stroke.

In the case of disfunctions after a stroke, the disfunctional zone surrounding the stroke focus is stimulated.

The device according to the invention can be used both as an implant for permanent therapy for the abovementioned neurological and psychiatric disorders and for intraoperative target point diagnosis, that is to say intraoperative finding of the optimum target point for the electrode implantation.

The invention claimed is:

1. A device, comprising:
   at least one electrode and/or at least one chip configured to stimulate cerebral neurons that have a pathological oscillatory activity with a period duration T;
   n contact points that are distributed over at least one electrode and/or over at least one chip and are configured to output electrical stimulus signals to the brain, where $n \geq 2$;
   a sensor configured to measure the pathological oscillatory activity of the cerebral neurons;
   a controller configured to drive the contact points to output the electrical stimulus signals in a succession of stimulation time periods during which the electrical stimulus signals are output and alternating pauses during which none of the contact points outputs electrical stimulus signals, wherein
   the sensor measures the pathological oscillatory activity of the cerebral neurons during one of the pauses and the controller lengthens the respective pause by the period duration T or an integral multiple of the period duration T when the pathological oscillatory activity of the cerebral neurons falls below a predetermined threshold value.

2. The device as claimed in claim 1, wherein the controller is configured to drive the contact points so that the contact points output a low-frequency succession of sequences of high-frequency pulse trains to the brain during the stimulation time periods, wherein, for each sequence, m contact points of the n contact points are selected, with $m \geq 2$ and $m < n$, and high-frequency pulse trains are applied only via the selected m contact points, and the temporal shift between two successive high-frequency pulse trains that are applied by different contact points is T/m.

3. The device as claimed in claim 2, wherein within the succession of sequences the selection of the m contact points is varied in one of a deterministic fashion, a stochastic fashion, and a combined deterministic-stochastic fashion.

4. The device as claimed in claim 2, wherein, for each sequence, an order of the selected m contact points, at which the selected m contact points output the high-frequency pulse trains, is selected.

5. The device as claimed in claim 4, wherein within the succession of sequences the selection of the order of the selected m contact points is varied in one of a deterministic fashion, a stochastic fashion, and a combined deterministic-stochastic fashion.

6. The device as claimed in claim 2, wherein time intervals between successive sequences are varied in one of a deterministic fashion, a stochastic fashion, and a combined deterministic-stochastic fashion.

7. The device as claimed in claim 2, wherein the period duration T of the pathological oscillatory activity in the case of Parkinson's disease is approximately 200 ms.

* * * * *

UNITED STATES PATENT AND TRADEMARK OFFICE
CERTIFICATE OF CORRECTION

| | | |
|---|---|---|
| PATENT NO. | : 8,116,874 B2 | Page 1 of 1 |
| APPLICATION NO. | : 11/812258 | |
| DATED | : February 14, 2012 | |
| INVENTOR(S) | : Peter Tass | |

It is certified that error appears in the above-identified patent and that said Letters Patent is hereby corrected as shown below:

On the Title Page

Item (73) (Assignee), Line 1, Delete "Forschungzentrum" and insert -- Forschungszentrum --, therefor.

Signed and Sealed this
Fourth Day of September, 2012

David J. Kappos
*Director of the United States Patent and Trademark Office*